(12) United States Patent
Tatenuma et al.

(10) Patent No.: US 11,849,731 B2
(45) Date of Patent: Dec. 26, 2023

(54) METHOD OF IMPARTING ANTIBACTERIAL AND DEODORANT FUNCTIONS AND MATERIALS TO WHICH THE ANTIBACTERIAL AND DEODORANT FUNCTIONS THEREOF IS IMPARTED

(71) Applicant: Kaken Co., Ltd., Mito (JP)

(72) Inventors: Katsuyoshi Tatenuma, Mito (JP); Yoshiaki Kinase, Mito (JP); Yuri Natori, Mito (JP); Junko Matsui, Mito (JP)

(73) Assignee: Kaken Co., Ltd., Mito (JP)

( * ) Notice: Subject to any disclaimer, the term of this patent is extended or adjusted under 35 U.S.C. 154(b) by 622 days.

(21) Appl. No.: 17/043,389

(22) PCT Filed: Jun. 10, 2020

(86) PCT No.: PCT/JP2020/022883
§ 371 (c)(1),
(2) Date: Sep. 29, 2020

(87) PCT Pub. No.: WO2021/059613
PCT Pub. Date: Apr. 1, 2021

(65) Prior Publication Data
US 2023/0103590 A1     Apr. 6, 2023

(30) Foreign Application Priority Data
Sep. 25, 2019   (JP) ................. 2019-173663

(51) Int. Cl.
*A01N 59/12* (2006.01)
*A01P 1/00* (2006.01)
*C09D 1/00* (2006.01)

(52) U.S. Cl.
CPC ............. *A01N 59/12* (2013.01); *A01P 1/00* (2021.08); *C09D 1/00* (2013.01)

(58) Field of Classification Search
CPC .................................................. A01N 59/12
See application file for complete search history.

(56) References Cited

U.S. PATENT DOCUMENTS
6,413,405 B1   7/2002  Jung

FOREIGN PATENT DOCUMENTS
JP     9-151106 A    6/1997
JP     2002-200424 A  7/2002
(Continued)

OTHER PUBLICATIONS

Onodera, Hayato, Chida, Taiji, and Niibori, Yuichi (Sorption Behavior of Iodate Ions on Calcium Silicate Hydrate under a High Saline Condition—18176. United States: N. p., 2018) (Year: 2018).*

(Continued)

*Primary Examiner* — Benjamin J Packard
(74) *Attorney, Agent, or Firm* — Crowell & Moring LLP

(57) ABSTRACT

Provided is a method of imparting antibacterial and deodorant functions by reacting iodic acid, and a material that is given antibacterial and deodorant functions. The method of imparting antibacterial and deodorant function is as follows. Reacting iodate to a material that includes elements capable of producing iodate insoluble in water and non-toxic to a living body to form iodic acid of such elements on the surface of the material, thereby the iodate is made to be supported so that antibacterial and deodorant is possible without elution of said iodate to the outside.

3 Claims, 5 Drawing Sheets

(56) References Cited

FOREIGN PATENT DOCUMENTS

| | | | |
|---|---|---|---|
| JP | 2002-542398 A | 12/2002 | |
| JP | 3423971 B2 | 7/2003 | |
| JP | 2020-125560 A | 8/2020 | |
| WO | WO-2017049453 A1 * | 3/2017 | ............. A01N 59/16 |

OTHER PUBLICATIONS

International Search Report (PCT/ISA/210) issued in PCT Application No. PCT/JP2020/022883 dated Aug. 25, 2020 (five (5) pages).

Japanese-language Written Opinion (PCT/ISA/237) issued in PCT Application No. PCT/JP2020/022883 dated Aug. 25, 2020 (four (4) pages).

* cited by examiner

| No. | Sample name | Antibacterial effect 5 (strong) to 0 (no efficacy) |
|---|---|---|
| 1 | [Iodox-C] $Ca(IO_3)_2$ | 5 |
| 2 | $Ca(IO_3)_2$/AC | 4 |
| 3 | [Iodox-B] $Ba(IO_3)_2$ | 5 |
| 4 | $Ba(IO_3)_2$/AC | 4 |
| 5 | [Iodox-A] $AgIO_3$ | 5 |
| 6 | $AgIO_3$/AC | 4 |
| 7 | TPE8g+$Ca(IO_3)_2$0.8g | 4 |
| 8 | TPE8g+$Ca(IO_3)_2$0.8g/AC | 1~2 |
| 9 | TPE8g+$Ca(IO_3)_2$0.2g | 3 |
| 10 | TPE8g+$Ca(IO_3)_2$0.2g/AC | 0~1 |
| 11 | TPE Ref | 0 |

2-hours impregnation with Iodox-N
(Iodine distribution image)

Fig. 5

Avian influenza virus inactivating effect of Iodox samples for 10 minutes

| Test sample | Half-amount reaction | | | Antiviral effect |
|---|---|---|---|---|
| | 1st test | 2nd test | 3rd test | |
| 1. Wet-Iodox calcium silicate grains Grain size 2 to 5 mm | ≧3.5* | ≧6.75 | 7.25 | - |
| 2-1. Iodox calcium silicate board [0 to 1 mm thick from the surface] | 2.5 | 3.5 | NT | 3 |
| 2-2. Iodox calcium silicate board [1 to 2 mm thick from the surface] | 4.75 | 4.0 | NT | 2 |
| 2-3. Iodox calcium silicate board [2 to 3 mm thick from the surface] | 4.75 | 4.25 | NT | 2 |
| 3. Iodox-C | 2.5 | ≧4.5 | 5.0 | |
| 4. Iodox-B | ≦0.5 | ≦0.5 | NT | 5 |
| Test virus | 7.75 | 7.5 | 7.25 | |

*: Residual virus titer (log10EID50/0.2 mL)    NT: Not tested

METHOD OF IMPARTING ANTIBACTERIAL AND DEODORANT FUNCTIONS AND MATERIALS TO WHICH THE ANTIBACTERIAL AND DEODORANT FUNCTIONS THEREOF IS IMPARTED

TECHNICAL FIELD

The present invention relates to a method of imparting antibacterial and deodorant functions by a reaction of iodic acid and further relates to materials that are given the antibacterial and deodorant functions thereof.

BACKGROUND ART

Iodic acid ($HIO_3$) is an oxo-acid of iodine (I). Iodic acid is a strong oxidizing substance and exerts antibacterial and deodorant functions against microorganisms such as bacteria and viruses. As described in Patent Document 1, an invention of a germicidal detergent composition in which hydrochloric acid is reacted with iodine ions and iodate ions and then dissolved in a nitric acid aqueous solution is also disclosed.

Iodic acid dissolves in water to generate iodate ion ($IO_3^-$), but its bactericidal power is impaired if it is diffused in water. Because of this, as described in Patent Literature 2, the inventor has also invented and applied for a patent an iodine-supporting material in which elemental iodine is supported on a material such as activated carbon. This patent-applied material is an iodine-supporting material that is non-invasive to living body and has a sustainable sterilizing power over a long time.

LITERATURE OF CONVENTIONAL ART

Patent Literature

Patent Literature 1

Japanese Patent No. 3423971

Patent Literature 2

Japanese Patent Application No. 2019-019044

SUMMARY OF INVENTION

Technical Problem

However, when iodine is supported on the powder of activated carbon, the activated carbon of such supporter may be scattered in the air or dispersed in water. Therefore, it is desired to directly impart functions such as antibacterial, antiviral, fungicide, insecticidal, and odor control or deodorant to materials such as fibers, fabrics, clothes, papers, synthetic resins, plastics, or building materials without using activated carbon or other similar materials.

Therefore, an object of the present invention is to provide a method for imparting antibacterial and deodorant functions by reacting iodic acid, and to provide materials having an antibacterial and deodorant function.

Solution to Problem

To solve the above problems, the present invention provides a method of imparting antibacterial and deodorant functions, which includes processing to react iodate compound to a material that includes an element capable of producing water-insoluble iodate and having no biotoxicity to the iodate, and the method further includes producing iodate of such element on the surface of such material to make the iodate to be supported enabling to do antibacterial and deodorant effects without elution of the iodate to the outside.

Further, in the method of imparting the antibacterial and deodorant functions, the above-mentioned element is any one of calcium, barium, and silver.

Still further, in the method of imparting the antibacterial and deodorant functions, the material is any one of calcium silicate, limestone, diatom earth, gypsum, and plastic.

Furthermore, the material having antibacterial and deodorant functions of the present invention is a material having antibacterial and deodorant effect given by the above-mentioned imparting method of antibacterial and deodorant functions.

Advantageous Effects of Invention

According to the present invention, antibacterial, antiviral, fungicide, insect-proof, odor control, or deodorant functions can be directly imparted by reacting iodic acid to materials such as textiles, fabrics, clothes, papers, synthetic resins, plastics, and building materials without intervening raw materials such as activated carbon that are easily scattered in the air or dispersed in water.

BRIEF DESCRIPTION OF DRAWINGS

FIG. 5 This is a figure showing the test results of the virus inactivating effect in the method of imparting antibacterial and deodorizing functions of the present invention.

DESCRIPTION OF EMBODIMENTS

Figure 1:
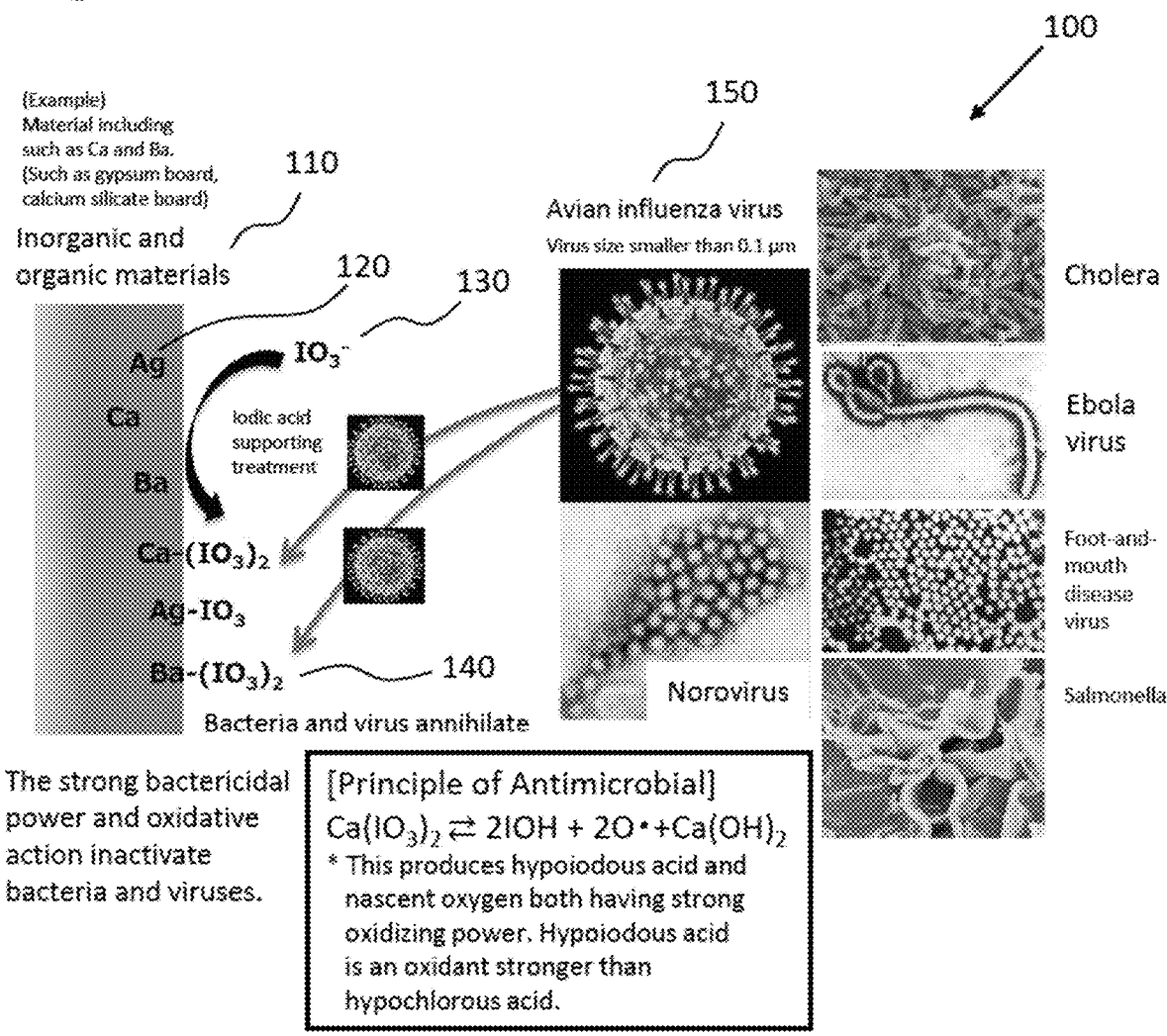
FIG. 1 This is a figure explaining the material to which the antibacterial and deodorizing functions are given by the method of imparting antibacterial and deodorizing functions of the present invention.

The following describes embodiments of the present invention in detail referring to the drawings.

It should, however, be noted that elements having the same function are denoted by the same reference numerals, and repeated description thereof may be omitted.

Example 1

As FIG. 1 shows, a method of imparting antibacterial and deodorant functions 100 includes processing to react an iodic acid compound 130 to a material 110 that includes an element 120 capable of producing a water-insoluble iodate 140 and having no biotoxicity to the iodate 140, and the method further includes producing iodate 140 of the element 120 on the surface of the material 110 to make the iodate 140 to be supported enabling to exert antibacterial and deodorant effects without elution of the iodate 140 to the outside.

The material 110 includes an inorganic material or an organic material such as fibers, fabrics, clothes, papers, synthetic resins, plastics, and building materials; a gypsum board and a calcium silicate board may be listed as examples. Examples further include inorganic filler dispersion type composite materials in which plastics such as polypropylene and limestone (mainly calcium carbonate) are mixed and synthetic paper made from limestone and high-density polyethylene. It should be noted that even powder of activated carbon or the like may be employed as long as it is fixed to a porous body such as fiber and does not scatter.

The gypsum board includes calcium sulfate ($CaSO_4$) as its main component and is used as a wall material having a high insulation performance for high heat and sound. Calcium silicate is a composition in which calcium oxide (CaO), silicon dioxide ($SiO_2$), water, etc. are combined in various proportions, and is obtained from limestone ($CaCO_3$) and diatom earth (mainly composed of silicon dioxide). The calcium silicate is used for building materials such as wall materials as a substance having excellent fire resistance and heat insulation.

The element 120, when reacted with the iodic acid compound 130, produces the iodate 140 that is hardly soluble in water and is not toxic to the living body. Examples of the element 120 include calcium (Ca), barium (Ba), and silver (Ag), etc. In addition, materials such as cadmium (Cd), lead (Pb) cannot be used in a general environment as they are toxic. The iodate 140 of these elements 120 includes calcium iodate ($Ca(IO_3)_2$), barium iodate ($Ba(IO_3)_2$), and silver iodate ($AgIO_3$).

Calcium iodate is stable in the air up to about 550° C. without thermal decomposition. The activated carbon supporting it is stable up to the activated carbon burning temperature (about 450° C.) in air. Further, barium iodate and silver iodate have the same tendency. In addition, calcium iodate is one of the act-specified mineral components as the nutritional components and other active ingredients of the feed according to an Act: "A feed additive designated by the Minister of Agriculture, Forestry and Fisheries based on the provisions of Article 2 Paragraph 3 of the Act on Safety Assurance and Quality Improvement of Feeds (Act No. 35 of 1953)". Therefore, it is not harmful even if the material is sprayed to a poultry house or livestock house as a disinfectant, or also even if a chicken or livestock licks the material used as a wall material of such houses as an antibacterial-effect-giving substance.

The iodic acid compound 130 inactivates microorganisms 150 such as bacteria and viruses by the strong bactericidal and oxidizing powers of iodate ions. Note that iodate ions also include per-iodate ions. The inactivation by iodate ion is exhibited by generating hypo-iodic acid and nascent oxygen both having strong oxidizing power. The inactivation is to kill the microorganisms 150 and to make the infectivity lose, and includes sterilization (virus), bacterial killing (virus), disinfection, bacteria elimination (virus), or antibacterial treatment (virus).

The microorganisms 150 are viruses, mycete (fungi), bacteria, and the like. The virus is about 50 nanometers (nm) in size and includes (bird) avian influenza virus, norovirus, Ebola virus, foot-and-mouth disease virus, human immuno-deficiency virus (HIV), and the like. It should be noted that a virus is not an organism by definition, but should be included in microorganisms 150. Mycete is a fungus having a size of about 5 micrometers (μm) and includes Trichophyton. Bacteria are about 1 micrometer (μm) in size and they include highly durable spore-forming bacteria such as *Bacillus subtilis* and *Bacillus natto*, and other general bacteria such as *Mycobacterium tuberculosis, Escherichia coli*, Cholera and *Salmonella*.

Iodine has considerably strong bactericidal power in the state of elemental iodine ($I_2$) and atomic iodine ($*I$) but loses bactericidal power in the state of iodine ion ($I^-$). In addition, the sterilizing power is maintained when the state of iodine is triiodide ion ($I3^-$), iodate ion ($IO3^-$), periodate ion ($IO4^-$), or another similar state. If the state is, however, water-soluble, their disinfecting power is impaired by the diffusion when dissolved in water.

Figure 2:
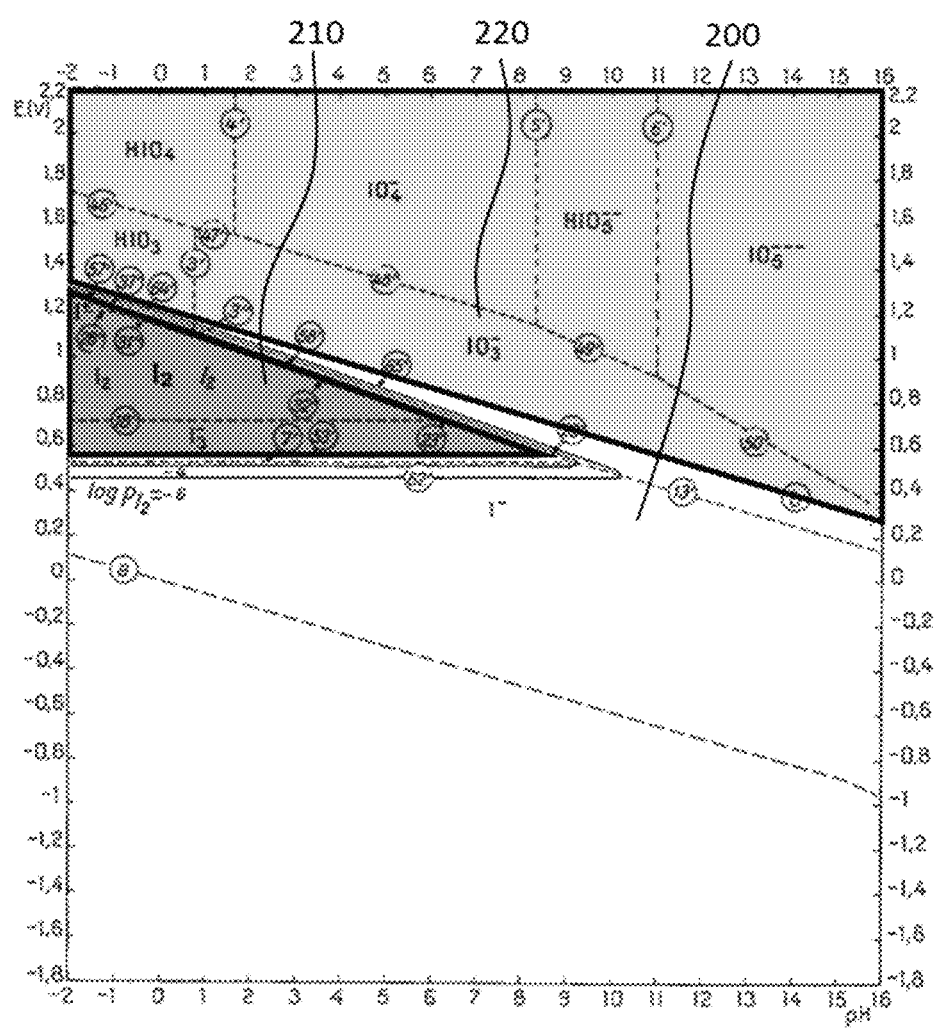
FIG. 2 This is a figure showing the active chemical status of the iodic acid used in the method of imparting antibacterial and deodorizing functions of the present invention.

As shown in FIG. 2, in region 200 in which the electric potential is in the reduction state, the state of iodine ions is present, therefore there is no antibacterial and antiviral effect. In the dark gray area 210 in the figure, if the pH (hydrogen ion concentration) is neutral to acidic, the state of elemental iodine is maintained, and there is an oxidizing power (antibacterial and antiviral effects). The effect lasts long because not water-soluble as well. It should be noted that when the pH becomes alkaline, the state becomes iodate ion state or iodine ion state.

In the light gray region 220 in the figure, the potential is in an extremely oxidative state and is in a state of iodate ion or the like. Therefore, its oxidative power (antibacterial and antiviral effects) is strong. If the iodate is insoluble in water, the state will be maintained in both acidic and alkaline environments, and the effect will last longer.

As shown in FIG. 1, the iodic acid compound 130 is supported by the material 110 by applying the iodic acid compound 130 to the material 110 in a manner: mixing, coating, spraying, or impregnating. The iodic acid compound 130 includes iodic acid ($HIO_3$), sodium iodate ($NaIO_3$), calcium iodate ($Ca(IO_3)_2$), barium iodate ($Ba(IO_3)_2$), and another similar substance.

For example, where a calcium silicate plate (the main component is $CaSiO_3$) used for a fireproof wall material is subjected to a treatment such as coating with sodium iodate (dilute hydrochloric acid or dilute sulfuric acid solution), an investigation of the surface product thereof using XRD (X-ray diffraction) method shows that calcium iodate has been produced on the surface of the calcium silicate plate, thereby its chemical properties are exhibited.

The iodate 140 of calcium, barium, silver, etc. is insoluble in water, is held stably without elution or volatilization to the outside of the material 110, is non-invasive to the living body, and maintains antibacterial power and the deodorizing power for a longer period.

Example 2

First, the antibacterial effect of iodic acid-treated silica particles was checked by BGLB (brilliant green lactose broth method). As a test bacterium, *E. coli* was used. The bacterial fluid was the suspension of the test bacterium ($10^5$ to $10^6$ CFU/mL) in the BGLB medium. Note that CFU is a colony-forming unit and is an index showing the number of viable cells.

Figures 3A, 3B:
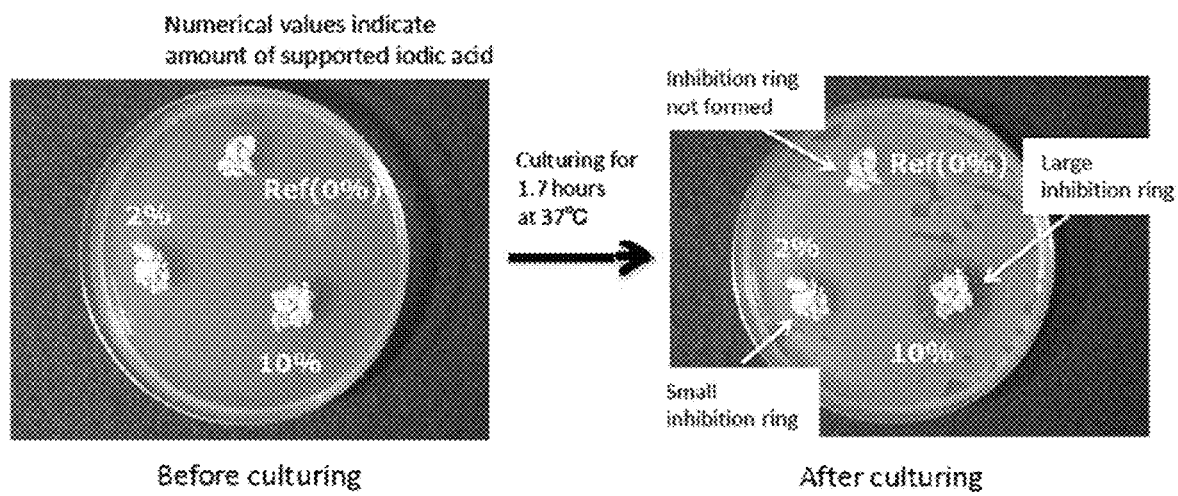
FIGS. 3A and 3B These are figures showing the test results of the antibacterial effect in the method of imparting antibacterial and deodorizing functions of the present invention.

Samples (1) to (11) shown in FIG. 3(a) were put in the bacterial solution contained in test tubes, and cultured at 37° C. for 22 hours. It was judged that the BGLB solution had an antibacterial effect if the solution had no foaming or turbidity. As shown in FIG. 3(a), the samples (1), (3), and (5), each treated with iodic acid, had an antibacterial effect. Further, samples (2), (4), and (6), each made to be supported on activated carbon (AC), also had an antibacterial effect.

The samples (7) to (10) mixed with the thermoplastic (TPE) exhibited antibacterial properties proportional to the mixing amount.

Next, a bacterial inhibition ring (halo) test was conducted on the calcium silicate particles treated with iodic acid. Dilute sulfuric solution of sodium iodate (10 g-$NaIO_3$/100 mL-dil $H_2SO_4$) was spray-coated on the calcium silicate particles (2 to 5 mm in size) so that the amount of iodate became 2.0 wt-% and 10 wt-%. That specimen was placed on a standard agar medium inoculated with *Escherichia coli* and cultured at 37° C. for 17 hours to observe the inhibition ring. As shown in FIG. 3(b), antibacterial properties depending on the amount of iodic acid applied were then confirmed.

Example 3

The calcium silicate plate was immersed in a sodium iodate solution (10 wt-%) in stages for 1 to 120 minutes, and the thickness of the surface reaction phase was measured with EDS (energy dispersive X-ray analysis method) to examine the distribution of iodic acid.

Figure 4A:
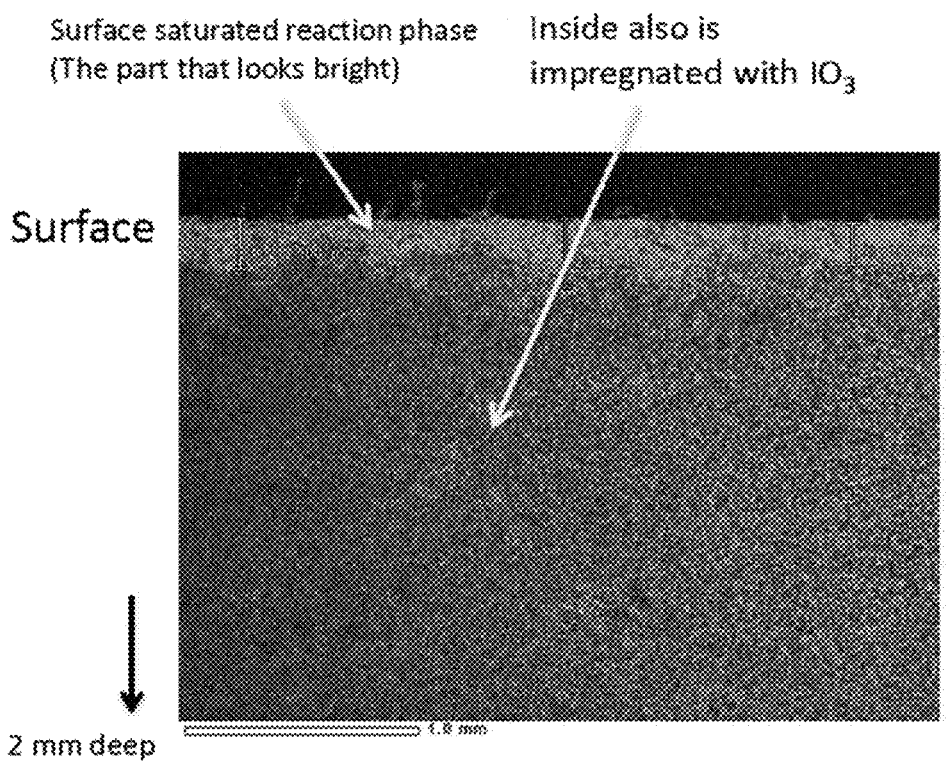
FIGS. 4A and 4B These are figures showing the test result of the antibacterial effect in terms of the thickness of the surface reaction phase in the method of imparting antibacterial and deodorizing functions of the present invention.
Figure 4B:
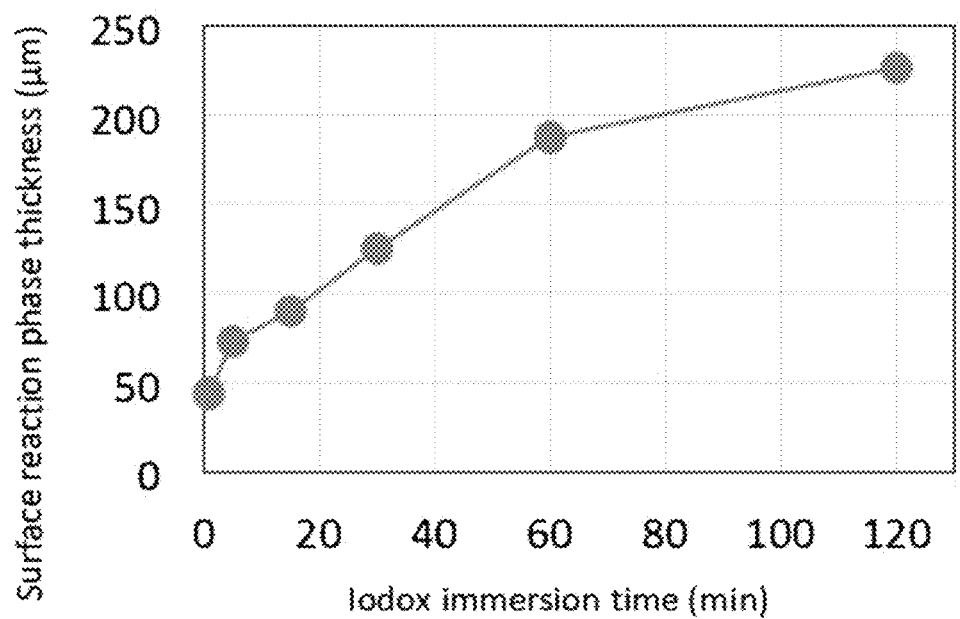

Two hours of immersion of a 6 mm thick calcium silicate plate caused the inner central portion of the plate to undergo the antibacterial treatment to the depth of 3 mm. As shown in FIG. 4(a), it is found that not only the surface reaction phase but also the inside is impregnated with iodic acid. Further, as shown in FIG. 4(b), the thickness of the surface reaction phase is almost proportional to the iodic acid treatment time. The presence of iodic acid was confirmed inside as well, thus the antibacterial property in the depth direction was also confirmed.

Example 4

Sodium iodate ($NaIO_3$) solution was sprayed on stubborn moldy bathroom tiles. Before the spraying, mold was present on the tile surface and its joints, but after that spraying, the mold disappeared, and the mold-prevention effect continued even after 6 months had passed. This is because sodium iodate reacts with the underlay of tile to form calcium iodate ($Ca(IO_3)_2$) imparting a permanent antifungal effect.

A patch test (pasting test) was conducted to determine whether it could cause contact dermatitis (rash). Powders of barium iodate ($Ba(IO_3)_2$), calcium iodate ($Ca(IO_3)_2$), and sodium iodate ($NaIO_3$) were brought into direct contact with the arm and that state was maintained. It was confirmed that no abnormality such as an allergic reaction was observed even when three kinds of powders were contact-exposed to the skin for 3 hours, and there was no invasiveness to the living body.

Example 6

The antiviral properties against pathogenic avian influenza virus were tested and evaluated. The materials put under the test were: calcium iodate, barium iodate, and a substance obtained by the reaction of iodic acid with plate-shaped and granular calcium silicate.

As an experimental material, the following specimens were used.
  (1) A specimen prepared by crushing wall material of 6 mm thickness (calcium silicate plate), sieving the crushes to 2 to 5 mm size silica particles, and spraying them with iodic acid,
  (2) A specimen intended for antibacterial and antiviral treatment of the wall material of livestock houses such as poultry and pig farming: prepared by dipping a calcium silicate plate (6 mm thick) in a solution of iodic acid, pulling up the plate 2 hours later, heating it at 110° C. to dry, scraping by a thickness of 0 to 1 mm from the dried plate surface to its central portion prepared as the experimental material (2-1), 1 to 2 mm as the material (2-2), 2 to 3 mm as the material (2-3), the shavings of which were collected for use.
  (3) A specimen prepared by separating, collecting, and dried precipitates produced by adding a sodium iodate solution to a calcium chloride solution,
  (4) A specimen prepared by separating, collecting, and drying precipitates produced by adding a sodium iodate solution to a barium chloride solution.

As the virus, avian influenza virus A/swan/Shimane/499/83 (H5N3) strain was used. This virus was inoculated into the allantoic cavity of 10-day-old embryonated chicken eggs and cultured at 35° C. for 2 days, and then allantoic fluid was collected and used as a virus solution. The virus solution was prepared to about $10^{7.5}$ $EID_{50}$/0.2 mL with PBS (phosphate-buffered saline) according to calculating the infectious titer of 50% embryonated chicken egg ($EID_{50}$). As for the chicken eggs used, SPF fertilized eggs were hatched and subjected to the test at 10 days of age.

400 mg of the experimental materials (1), (4), and (5); and 200 mg of the materials (2-1), (2-2), and (2-3) were weighed and mixed with half of each weight of virus solution, then allowed them to react at room temperature for 10 minutes. After the reaction, SCDLP (lecithin polysorbate 80-added soybean casein digest) medium was added and the reaction was terminated by adding 10-fold dilution. Then, the cells were diluted 10-fold with PBS in stepwise, and 0.2 mL of PBS-diluted cells were inoculated into three 10-day-old embryonated allantoic cavities at each dilution step, followed by culturing at 35° C. for 2 days. After culturing, allantoic fluid was collected and allowed to react with 0.5% chicken red blood cell suspension, and the presence or absence of virus growth was determined by the agglutination of red blood cells. The residual virus titer was calculated in terms of $EID_{50}$ by the Reed-Muench method.

As shown in FIG. 5, in the experimental material (4), the residual virus titer reduced to about 1/5,000,000 or less. In the experimental material (2-1), the titer reduced to about 1/50,000. In (2-2) and (2-3), the titer reduced to about 1/1,000. In material (3), titer was reduced to about 1/5,000 (1/150 or less), however, the effect had fluctuation.

As for the experimental material (1), the solution of iodic acid was treated only by spraying, and the reaction accelerating treatment such as the heating treatment after the spraying was not carried out. Therefore, the impregnated site was uneven, and the stable antiviral property could not be confirmed. As for the materials (2-1) to (2-3), it was observed that the treatment effect of iodic acid has a tendency of dependency on the thickness of the calcium silicate plate, and 2 hours of such treatment made it possible to spread the efficacy range of the antibacterial treatment effect up to the central portion. The material (4) showed a very strong antiviral property.

According to the present invention, by reacting iodic acid with materials such as fibers, cloth, clothes, papers, synthetic resins, plastics, or building materials without using materials such as activated carbon that are easily scattered in the air or dispersed in water, it becomes possible to directly give functions such as antibacterial, antivirus, mildew-proof, insect-proof, deodorant, or deodorant to those materials.

Although the examples of embodiment of the present invention have been described above, the embodying mode of the present invention is not limited thereto.

REFERENCE SIGNS LIST

100: Method of imparting antibacterial and deodorant functions
110: Material
120: Element
130: Iodic acid compound
140: Iodate
150: Microorganisms
200: Area (Iodine ion)
210: Area (elemental iodine)
220: Area (iodic acid ion)

The invention claimed is:

1. A method of imparting antibacterial and deodorant functions to a material that is capable of producing iodate insoluble in water and non-toxic to a living body,
    wherein imparting is performed by reacting an iodic acid compound to said material by way of mixing, coating, spraying, or impregnating to form a surface reaction phase on the surface layer of said material, and
    wherein said surface reaction phase is an iodate changed from said material making said iodate to be supported so that antibacterial and deodorant is possible without use of activated carbon and elution of said iodate to the outside of said material.

2. The method of imparting antibacterial and deodorant functions according to claim 1, wherein said material is either calcium silicate, diatom earth, or gypsum.

3. A material that is imparted antibacterial and deodorant functions by the method as claimed in claim 1.

* * * * *